(12) United States Patent
Stanley et al.

(10) Patent No.: US 10,441,257 B2
(45) Date of Patent: *Oct. 15, 2019

(54) VASCULAR CLOSURE DEVICE SUTURE TENSION LIMITING AND INDICATION MECHANISM

(71) Applicant: Cook Medical Technologies LLC, Bloomington, IN (US)

(72) Inventors: Cleon Stanley, Bloomington, IN (US); Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/468,875

(22) Filed: Mar. 24, 2017

(65) Prior Publication Data

US 2017/0189001 A1 Jul. 6, 2017

Related U.S. Application Data

(63) Continuation of application No. 14/180,625, filed on Feb. 14, 2014, now Pat. No. 9,642,605.

(60) Provisional application No. 61/787,209, filed on Mar. 15, 2013.

(51) Int. Cl.
*A61B 17/00* (2006.01)
*A61B 17/04* (2006.01)
*A61B 90/00* (2016.01)

(52) U.S. Cl.
CPC ............ *A61B 17/0057* (2013.01); *A61B 2017/00623* (2013.01); *A61B 2017/00654* (2013.01); *A61B 2017/00659* (2013.01); *A61B 2017/00862* (2013.01); *A61B 2090/064* (2016.02); *A61B 2090/0807* (2016.02)

(58) Field of Classification Search
CPC ...... A61B 17/0057; A61B 2017/00862; A61B 2017/00623; A61B 2017/00659; A61B 2017/00654

See application file for complete search history.

(56) References Cited

U.S. PATENT DOCUMENTS

| 5,021,059 A | | 6/1991 | Kensey et al. | |
| 5,129,912 A | | 7/1992 | Noda et al. | |
| 5,350,399 A | * | 9/1994 | Erlebacher | A61B 17/0057 128/899 |
| 5,411,520 A | * | 5/1995 | Nash | A61B 17/0057 128/887 |

(Continued)

*Primary Examiner* — Julian W Woo
(74) *Attorney, Agent, or Firm* — Woodard, Emhardt, Henry, Reeves & Wagner, LLP

(57) ABSTRACT

An apparatus and system that includes an elongated body, a vascular closure device that can occlude a hole in a vessel wall coupled to a distal end of the elongated body, a sleeve assembly and a biasing member arranged to elastically deform coupled between the elongated body and the sleeve assembly, wherein the vascular closure device is pliant and is deformable to fit with the sleeve assembly but is too large to fit within the sleeve assembly without deforming it and where application of tension to the elongated body by retracting the sleeve assembly away from the deployed vascular closure device elastically deforms the biasing member and exerts a force on the vascular closure device.

22 Claims, 15 Drawing Sheets

(56) References Cited

U.S. PATENT DOCUMENTS

| | | | |
|---|---|---|---|
| 5,593,422 A * | 1/1997 | Muijs Van de Moer | A61B 17/0057 604/285 |
| 5,830,231 A | 11/1998 | Geiges, Jr. | |
| 6,045,569 A | 4/2000 | Kensey et al. | |
| 6,059,800 A | 5/2000 | Hart et al. | |
| 6,090,130 A | 7/2000 | Nash et al. | |
| 6,409,739 B1 | 6/2002 | Nobles et al. | |
| 6,860,895 B1 * | 3/2005 | Akerfeldt | A61B 17/0057 606/139 |
| 7,204,841 B2 | 4/2007 | Green | |
| 7,390,329 B2 | 6/2008 | Westra et al. | |
| 7,850,710 B2 | 12/2010 | Huss | |
| 9,307,967 B2 | 4/2016 | Tegels et al. | |
| 9,314,230 B2 | 4/2016 | Roorda et al. | |
| 9,486,162 B2 | 11/2016 | Pipenhagen | |
| 9,492,156 B2 | 11/2016 | Tegels | |
| 9,642,605 B2 * | 5/2017 | Stanley | A61B 17/0057 |
| 2010/0286727 A1 | 11/2010 | Terwey | |
| 2015/0068009 A1 * | 3/2015 | Walters | A61B 17/0057 29/407.08 |

\* cited by examiner

VASCULAR CLOSURE DEVICE SUTURE TENSION LIMITING AND INDICATION MECHANISM

CROSS REFERENCE TO RELATED APPLICATIONS

The present application is a continuation of U.S. patent application Ser. No. 14/180,625 filed Feb. 14, 2014, issued as U.S. Pat. No. 9,642,605, which claims the benefit of U.S. Provisional Patent Application, Ser. No. 61/787,209 filed Mar. 15, 2013, which is hereby incorporated by reference.

FIELD

The present disclosure relates generally to systems and methods for sealing an opening in the body of a patient.

BACKGROUND

This disclosure concerns apparatuses and methods useful for sealing an opening in a body wall, such as an access opening in the wall of a blood vessel or a fistula. In particular, apparatus and methods are disclosed for closing and allowing healing of an opening in a tissue wall, whether made during a medical procedure (e.g. those in which apparatus or medicaments are introduced into tissue) or naturally occurring (e.g. as a result of malformation or disease).

It has long been known to insert devices into bodily vessels or conduits to provide therapy or for diagnostic purposes. For example, in cardiovascular medicine, it is known to insert catheters, stents and other devices into a patient's vascular system in order to evaluate or treat the patient. In the case of percutaneous transluminal angioplasty (PTA), an opening is made through the patient's skin and into a large or relatively large blood vessel, such as the femoral artery, and a balloon is inserted into the vessel and advanced to the location where vessel narrowing has occurred, such as by atherosclerosis. Similar procedures are used to implant stents to maintain flow through blood or other bodily vessels or ducts. In accessing the interior of a blood vessel, the interventionist or medical professional may breach the integrity of the vessel. A variety of devices (e.g. needles, guide wires, cannula) are known to open a path into a vessel via a percutaneous opening or other approach. Additional devices or implants can be moved through such devices, or through sleeves or cannula placed in the opening to keep it open, and into the vessel.

When the procedure is concluded, a cannula or other access device is removed from the vessel, leaving an opening in the vessel. If the arteriotomy is not adequately closed, a subcutaneous hematoma will form. The medical professional may therefore take steps to close the opening in the vessel. In some cases, the opening may be sutured closed, but such action can be very difficult in close quarters, and many vessel-accessing procedures are intended to be minimally-invasive to reduce tissue damage. It is also known to apply constant, firm external pressure to the opening in the vessel, particularly if it is a blood vessel, to allow the body's natural coagulation and healing processes to work. In cases in which angioplasty or similar treatment has taken place, however, commonly an anticoagulant has been administered to the patient, making natural closing of the opening in the vessel wall a longer or more difficult process. Maintaining physical pressure on a relatively large blood vessel for a time period sufficient for natural closure also presents at least inconvenience and discomfort to the patient in having to remain motionless and submit to that pressure, and there is the risk that too much pressure can damage the vessel or tissues that rely on continued flow through it.

Therapies for closing naturally-occurring fistulae or other undesirable bodily openings are also known. Treatments have included closure by suturing or by covering the opening, and by other surgical techniques. Frequently these therapies have required open surgeries with their attendant difficulties.

Devices have been created for inserting closures into a blood vessel or on its exterior that are designed to block the opening and/or soak up fluids that escape the vessel, or are present in the opening through the skin leading to the vessel. Such devices have, however, proven unsatisfactory in many respects, as have therapies for closing naturally-occurring openings in tissue. Needs therefore exist for improved and/or alternative devices and systems for inserting a closure for an opening in tissue that produces a seal without significantly blocking adjacent flow where desired (e.g. through a blood vessel), and fills the opening where that is desirable.

SUMMARY

In certain aspects, the present disclosure provides an apparatus that includes a sleeve assembly having a bore that is adapted to be inserted into an introducer, a pliant vascular closure device that deforms to fit within a bore of the sleeve assembly, an elongated body couple to the vascular closure device and a biasing member that connects the elongated body to the sleeve assembly so when the vascular closure device is deployed with a vessel in the body of the patient, retracting the sleeve assembly away from the patient's body applies tension to the elongated body and elastically deforms the biasing member and exerts a force on the vascular closure device.

Application of a conforming force through the elongated body may deform the vascular closure device against the vessel wall. Conforming the vascular closure device against the vessel wall may fluidly seal the vessel wall. The vascular closure device may be dome shaped. The sleeve assembly may include a flange that abuts the introducer so that the introducer may be gripped to retract the sleeve assembly.

The biasing member may be substantially more pliant than either the elongated body or the sleeve assembly. The elongated body may optionally include an indicator located on the elongated body to be obscured when the elongated body is not displaced with respect to the sleeve assembly and discernible when a conforming force is applied to the elongated body through the biasing member and the sleeve assembly. The indicator may optionally include a conforming graduation and/or a distorting graduation that indicates when either a conforming force or a distorting force is applied to the vascular closure device.

The biasing member may be a compressible member positioned between the sleeve assembly and an end protrusion on the elongated body or the biasing member may be a tensile member positioned on the end of the elongated body.

The sleeve assembly may define a bore that can hold the vascular closure device and the elongated body while permitting longitudinal displacement of the vascular closure device and the elongated body with respect to the sleeve assembly.

A packing member may optionally be arranged on the elongated member. The packing member may be longitudinally displaceable with respect to the elongated member.

The sleeve assembly may be configured to be insertable into the lumen of an introducer sheath, such as an introducer sheath used to gain access to blood vessels.

Further forms, objects, features, aspects, benefits, advantages, and embodiments of the present invention will become apparent from a detailed description and drawings provided herewith.

DESCRIPTION OF THE ILLUSTRATED EMBODIMENTS

Figure 1:
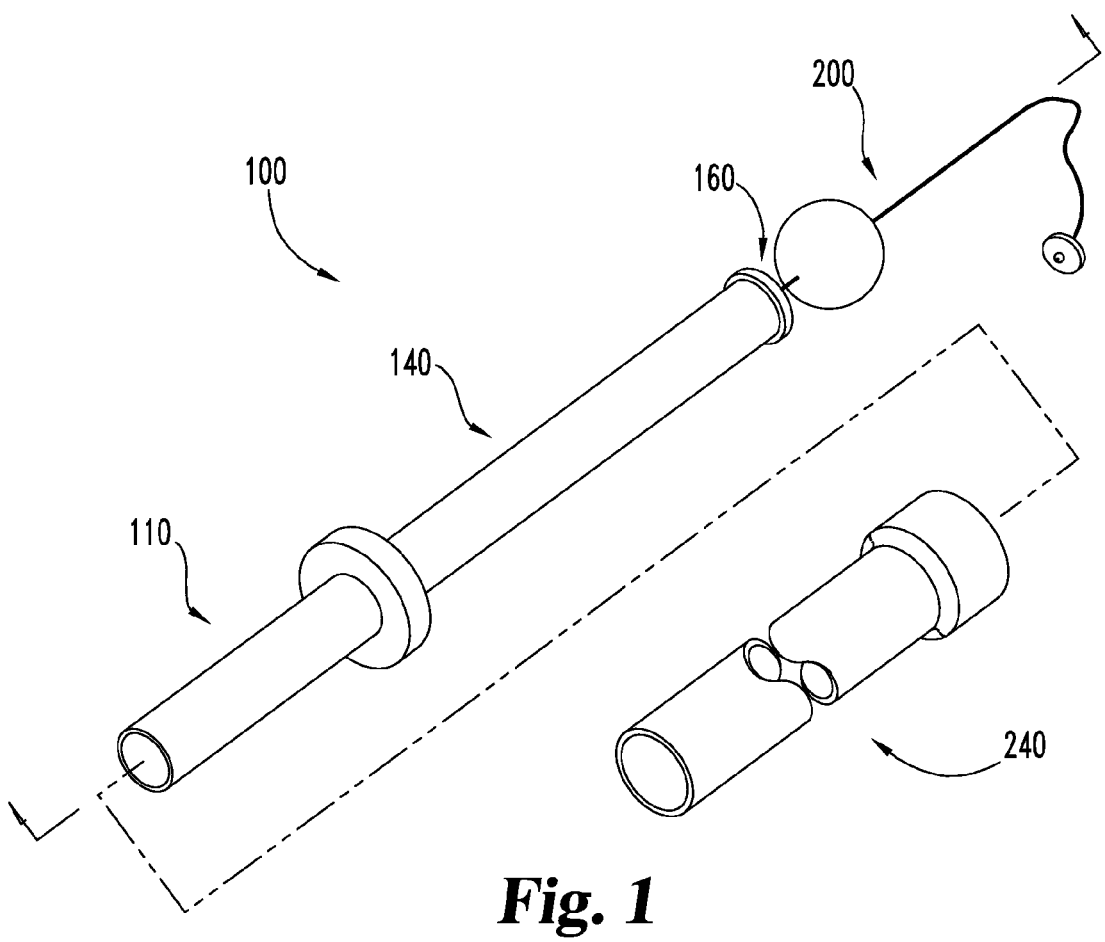
FIG. 1 is a perspective view of an embodiment of a system for closing a hole in a vessel wall, the system including a biasing member, a packing member, an elongated body, a sleeve and a vascular closure device.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With respect to the specification and claims, it should be noted that the singular forms "a", "an", "the", and the like include plural references unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The description below will focus on use in blood vessels of a human or animal, but it will be understood that the structures disclosed herein have application to a number of other vessels or conduits or bodily cavities. Closure or treatment of undesired openings in a variety of tissues can be performed with structures and methodology as disclosed. Examples of other applications include sealing primary and/or secondary openings of a fistula with healing or correction (e.g., filling) of the fistula between the openings. Such fistulae may include vesicovaginal fistulae, which are abnormal passages between the vagina and bladder.

Figure 2:
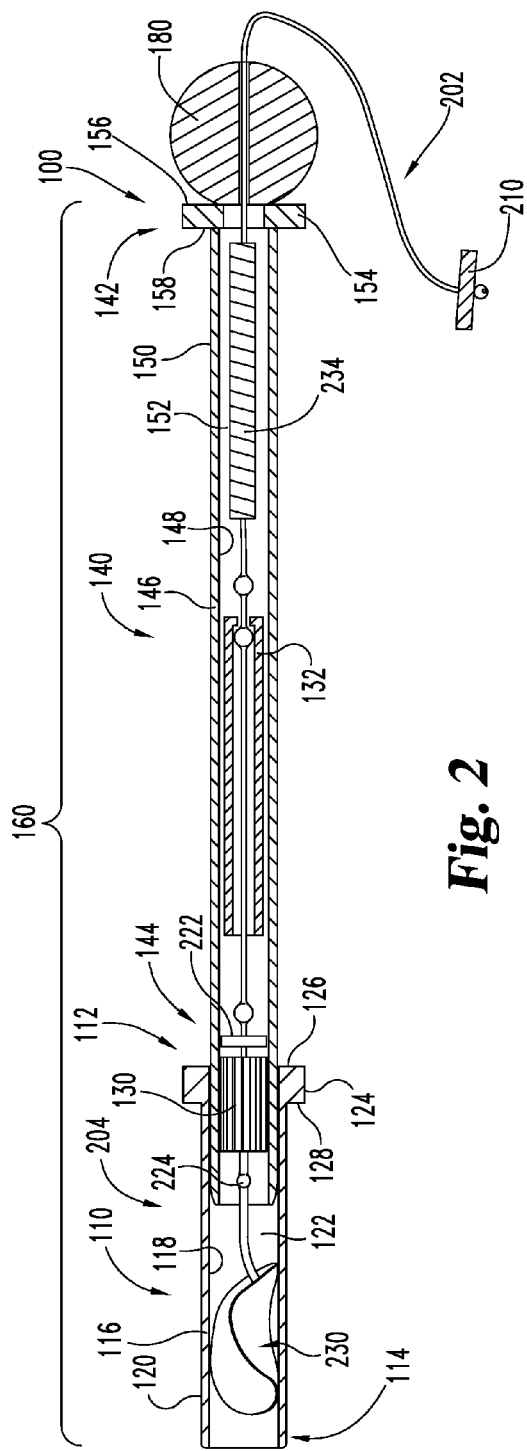
FIG. 2 is a cross-sectional view of the system illustrated in FIG. 1.

Referring now to FIGS. 1 and 2, system 100 for closing an opening in a wall of a vessel, conduit or other bodily cavity is illustrated. System 100 includes sleeve assembly 160, elongated body 200, and, in some instances, packing member 130, pushing member 132, vascular closure device 230 and introducer 240.

In the illustrated embodiment, sleeve assembly 160 includes outer sheath 110 and an insertion sheath 140. Outer sheath 110 has proximal end region 112, distal end region 114 and wall 116. Wall 116 has inner surface 118 and outer surface 120. Inner surface 118 defines lumen 122 that is constructed and arranged to receive vascular closure device 230 and/or insertion sheath 140. Insertion sheath 140 includes proximal end region 142, distal end region 144, and wall 146 having inner surface 148 and outer surface 150.

Inner surface 148 of wall 146 defines lumen 152 constructed and arranged to retain elongated body 200 of system 100. Outer surface 150 is constructed and arranged to slidably couple with inner surface 118 of wall 116 of outer sheath 110 so as to allow insertion sheath 140 to slide within lumen 122 of outer sheath 110.

Wall 116 also forms a flange 124 on outer surface 120 positioned near proximal end region 112 of outer sheath 110. Flange 124 defines proximal surface 126 and distal surface 128. Wall 146 of insertion sheath 140 defines flange 154 having proximal surface 156 and distal surface 158. Proximal surface 126 and distal surface 158 are constructed and arranged to limit the distance that insertion sheath 140 is insertable into outer sheath 110.

Elongated body 200 is a flexible body constructed for transferring tensile loads. Elongated body 200 may be a single strand of material or elongated body 200 may include one or more plies or strands that may be twisted or braided together. Elongated body 200 may be a generally solid body manufactured or molded to a desired shape. Elongated body 200 is comparatively ridged in tension but may be too flexible to provide compressive strength. Elongated body 200 may be a type of suture material or a variety of other elongated materials capable of extending within a body passageway, vessel or cavity, including various biodegradable and non-biodegradable cords, filaments, chains, strings, elongate graft members, wires and other similar objects having relatively slender profiles for extending through a tract or other passageway or void in patient tissue. In some instances, a somewhat heftier elongated structure such as a generally solid biodegradable or non-biodegradable three-dimensional body may be made to extend through a bodily opening or passageway. Such a structure may have more heft and bulk than a thread or filament.

Vascular closure device 230 may be affixed to distal end region 204 of elongated body 200. Vascular closure device 230 may be a separate component from elongated body 200 or vascular closure device 230 may be unitarily constructed with elongated body 200. Vascular closure device 230 may be any implement used to cover and occlude a hole 1016 in a vessel wall. As will be apparent to one of ordinary skill in the art, a variety of vascular closure devices 230 may be used with the disclosed systems. For example, a domed-shaped sealing member 232 having a semi-elliptical shape in an unstressed configuration may be used. As will be appreciated by one of ordinary skill in the art, vascular closure devices 230 may have different shapes, different dimensions, different materials, and/or different properties. System 100 may be constructed to position and conform a vascular closure device 230 that may be left in situ after a procedure.

Biasing member 180 is a pliant body located between elongated body 200 and sleeve assembly 160. As shown in FIG. 2, biasing member 180 is spherical with passage for elongated body 200 to pass through. Biasing member 180 is positioned on elongated body 200 between protrusion 210 and sleeve assembly 160. Biasing member 180 is constructed and arranged to act as a spring when compressed between protrusion 210 and proximal surface 156 as described below. Specifically, biasing member 180 is constructed of an elastic material that can elastically deform when compressed as described. For example, biasing member 180 may be constructed from a soft rubber, silicone or an elastomeric material. When compressed, biasing member 180 exerts a force substantially proportional to the displacement of biasing member 180 that seeks to return biasing member 180 to its unstressed state, as illustrated in FIG. 2.

Biasing member 180 may be constructed and arranged such that the amount of force required to compress a particular biasing member 180 is substantially equivalent to a conforming force for a particular vascular closure device 230. Biasing member 180 may be varied to account for a specific vascular closure device 230 used in conjunction with a particular biasing member 180.

Elongated body 200 includes protrusion 210 located in proximal end region 202 of elongated body 200. Protrusions 210 can be of a variety of shapes, including barbs, knots, frusto-conical segments, or flat surfaces, to name a few non-limiting examples. Additionally, protrusion 210 may be made monolithically with elongated body 200 or separate from elongated body 200 and coupled to it later. Protrusion 210 may be affixed to elongated body 200 or protrusion 210 may be slidingly engaged on elongated body with protrusion 212 on elongated body 200 keeping protrusion 210 on the end of elongated body 200.

Elongated body 200 may include a locking member 222 positioned near distal end region 204. Locking member 222 may be constructed and arranged to secure a second vascular closure device positioned against outer surface 1012 of a vessel wall 1008 (opposite of vascular closure device 230) and/or to secure a packing member 130 in and/or around hole 1016 in vessel wall 1008. In many embodiments, locking member 222 is constructed and arranged so as to be capable of sustaining a conforming force between vascular closure device 230 and packing member 130.

Elongated body 200 may optionally include indicator 234. Indicator 234 may be an integral part of elongated body 200 or indicator 200 may be coupled to elongated body 200. Indicator 234 occupies a fixed relative longitudinal position on elongated body 200 and is arranged to become discernible to an operator when biasing member 180 is deformed, for example, by protruding from the end of sleeve assembly 160.

Elongated body 200 coupled to vascular closure device 230 is constructed and arranged so as to be capable of applying a conforming force to vascular closure device 230. The conforming force is an amount of force that conforms vascular closure device 230 to inner surface 1010 of vessel wall 1008, such that vascular closure device 230 substantially occludes hole 1016 in vessel wall 1008 and substantially seals hole 1016 to prevent or substantially reduce any blood from escaping vessel 1006.

Figure 3:
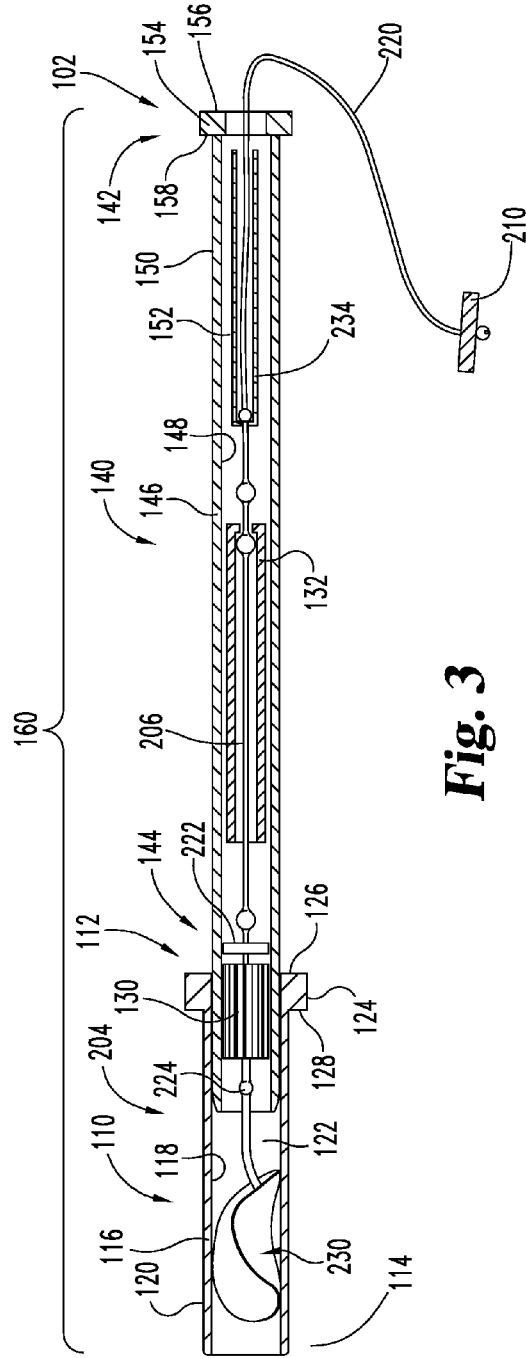
FIG. 3 is a cross-sectional view of the system illustrated in FIG. 1 incorporating an alternative embodiment of the biasing member.

Illustrated in FIG. 3 is system 102 an alternative embodiment of system 100. System 102 is similar to system 100 and shares many components, which are referenced using the same reference numerals used in FIG. 2 to refer to system 100. The major difference between systems 102 and 100 is that, in system 102, biasing member 180 is omitted and is replaced with elastic region 220 on elongated member 200. Elastic region 220 is located on elongated member 200 between protrusion 210 and indicator 234. Rigid region 206 represents the remaining portion of elongated member and includes at least the region between indicator 234 and vascular closure device 230. Elastic region 220 is substantially more pliant than rigid region 206. Elastic region 220 is constructed to elastically deform when tension is applied such that elastic region 220 lengthens longitudinally when tensioned and exerts a counter force that is approximately proportional to the relative longitudinal lengthening of elastic region 220. Elastic region 220 may be made of a soft rubber, silicone or elastomeric monofilament for example. System 102 otherwise functions in a similar way as described herein with regard to system 100.

Figure 4:
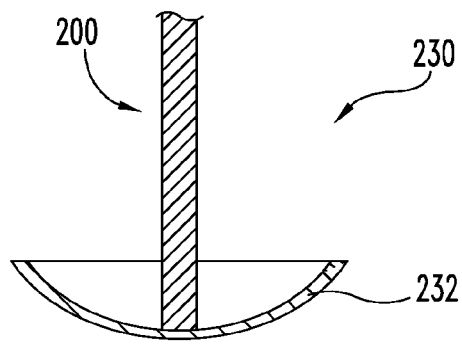
FIG. 4 is a cross-sectional side view of a vascular closure device coupled to an elongated body in an unconformed configuration.
Figure 5:
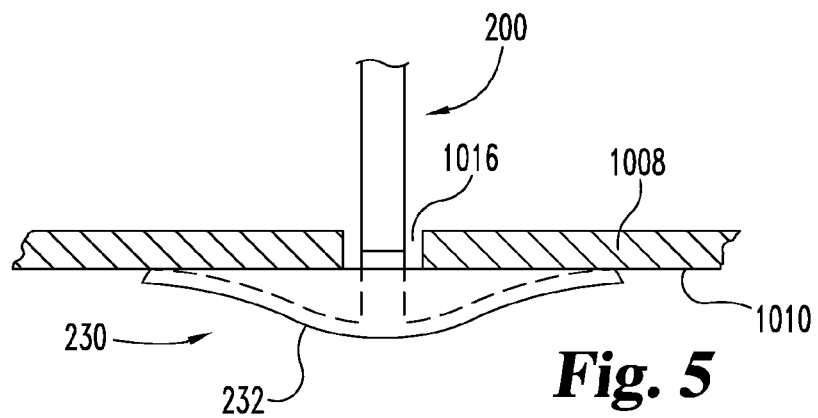
FIG. 5 is a side elevational view of the vascular closure device of FIG. 4 under a conforming force.

Illustrated in FIG. 4 is vascular closure device 230 in an unstressed configuration. As a conforming force is applied to vascular closure device 230 by elongated body 200, vascular closure device 230 deforms into a conforming configuration, as illustrated in FIG. 5. Vascular closure device 230 may be constructed and arranged such at the conforming configuration illustrated in FIG. 5 substantially seals hole 1016 to prevent or substantially reduce any liquid, such as blood, from passing through hole 1016.

Figure 6:
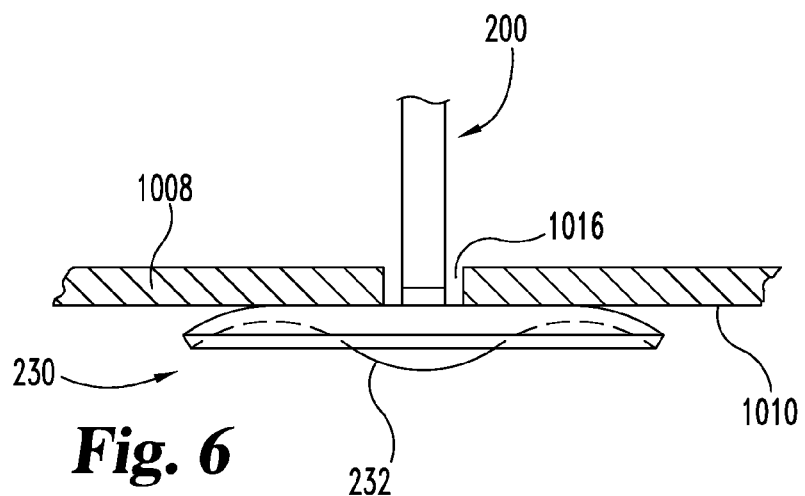
FIG. 6 is a side elevational view of the vascular closure device of FIG. 4 under a deforming force.
Figure 7:
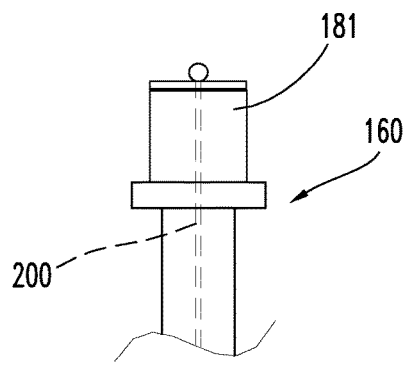
FIG. 7 is a side elevational view of a second alternate embodiment of the FIG. 1 biasing member.
Figure 8:
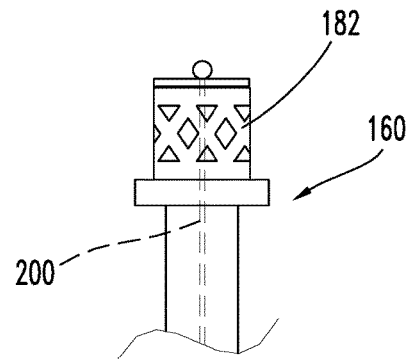
FIG. 8 is a side elevational view of a third alternate embodiment of the FIG. 1 biasing member.
Figure 9:
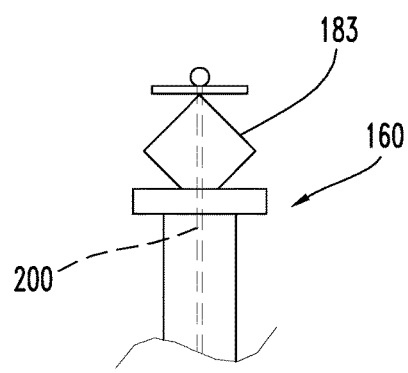
FIG. 9 is a side elevational view of a fourth alternate embodiment of the FIG. 1 biasing member.
Figure 10:
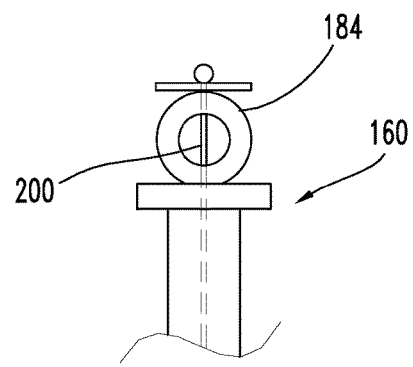
FIG. 10 is a side elevational view of a fifth alternate embodiment of the FIG. 1 biasing member.
Figure 11:
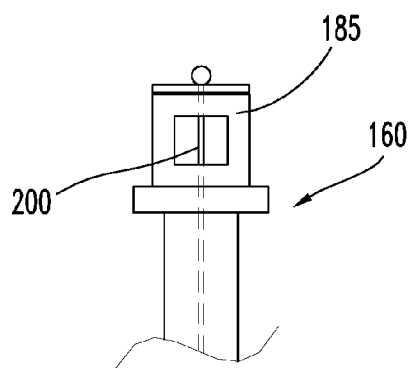
FIG. 11 is a side elevational view of a sixth alternate embodiment of the FIG. 1 biasing member.
Figure 12:
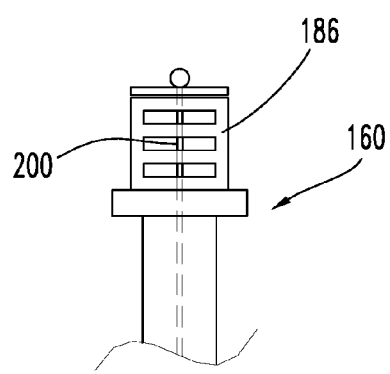
FIG. 12 is a side elevational view of a seventh alternate embodiment of the FIG. 1 biasing member.
Figure 13:
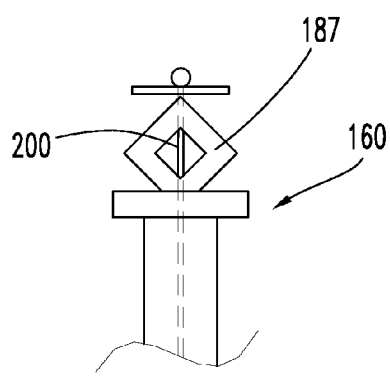
FIG. 13 is a side elevational view of an eighth alternate embodiment of the FIG. 1 biasing member.
Figure 14:
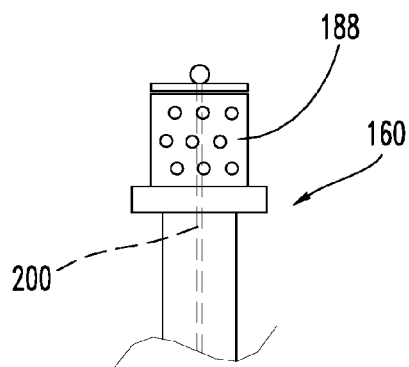
FIG. 14 is a side elevational view of a ninth alternate embodiment of the FIG. 1 biasing member.

FIG. 6 illustrates a deformed configuration that may or may not substantially seal hole 1016. The amount of force applied to vascular closure device 230 illustrated in FIG. 6 is greater than the amount of force applied to vascular closure device 230 illustrated in FIG. 5. FIGS. 5 and 6 illustrate varying ranges of deformation that may be applied to vascular closure device 230 while substantially sealing hole 1016. It should be understood that FIGS. 4-6 show exaggerated forms of vascular closure device 230 for illustrative purposes. Other vascular closure devices (not illustrated) having varying shapes as appropriate for particular applications may be used with system 100. It should also be understood that FIGS. 4-6 illustrate only a linear cross-section of vessel wall 1008. In use, vascular closure device may interact with a more complex geometry, such as a cylindrical vessel, causing the geometry of the vascular closure device to substantially conform to a complex shape.

A force that is greater than the conforming force can be applied to vascular closure device 230 through elongated body 200. For purposes of this application, such a force is referred to as a distorting force. A distorting force is the lesser of the amount of force necessary to deform vascular closure device 230 beyond a shape that occludes hole 1016 in vessel wall 1008, the amount of force necessary to pull vascular closure device 230 through hole 1016 in vessel wall 1008, and/or the amount of force necessary to damage vascular closure device 230 and/or vessel wall 1008. In some conditions, the deformed configuration of vascular closure device 230 illustrated in FIG. 6 may be a distorting force. In other conditions, the deformed configuration of vascular closure device 230 illustrated in FIG. 6 may be a conforming configuration.

FIGS. 7-14 illustrate alternative embodiments of biasing member 180 including biasing member 181, biasing member 182, biasing member 183, biasing member 184, biasing member 185, biasing member 186, biasing member 187 and biasing member 188. Biasing members 181, 182, 183, 184, 185, 186, 187 and 188 are alternative geometries for biasing member 180 that can be used, in conjunction with material selection, to adjust the amount of force that can be exerted by biasing member 180 and the deformation distance available.

FIGS. 1 and 15-24 illustrate an embodiment of introducer 240 that may be included in system 100 or introducer 240 may be a third party catheter introducer, for example. Introducer 240 comprises a proximal end region 242, a distal end region 244 and a wall 264 having an inner surface 248 and an outer surface 250. Inner surface 248 defines a lumen 252. Outer sheath 110, insertion sheath 140, and/or vascular closing device 230 are constructed and arranged to be insertable into lumen 252. In some instances, introducer 240 may include seal member 254, such as a hemostasis valve, positioned in proximal end region 242.

In some embodiments, system 100 includes packing member 130, pushing member 132, and locking member 222, each disposed in a sliding arrangement on elongated body 200. Packing member 130 may be positioned within insertion sheath 140 proximal to vascular closure device 230, and surrounding elongated body 200. Packing member 130 and locking member 222 are slidably engaged over elongated body 200 and pushing member 132 is arranged for an operator to apply force to locking member 222 against packing member 130 to move packing member 130 against outer surface 1012 of vessel wall 1008.

In the embodiments including locking member 222, locking member 222 may be used to retain packing member 130 in position against vessel wall 1008. Locking member 222 may be constructed and arranged to engage elongated body 200 in a manner that secures locking member 222 from moving along elongated body 200 in a proximal direction. For example, locking member 222 may engage a portion of elongated body 200 in distal end region 204 and apply a compressive force to packing member 130. In some instances, locking member 222 may engage protrusion 224 in distal end region 204 of elongated body 200. As packing member 130 is moved adjacent to outer surface 1012 of vessel wall 1008 by relative movement of pushing member 132, locking member 222 may pass over a portion of packing member 130 that resists proximal movement of locking member 222 and packing member 130 away from vessel wall 1008. In other embodiments, locking member 222 may be constructed to permit relative movement with elongated body 200 in a single direction only. In such an embodiment, features such as protrusion 224 may optionally be omitted. System 100 may be constructed and arranged such that the force that packing member 130 exerts on locking member 222 is communicated through elongated body 200 to vascular closure device 230 to retain vascular closure device 230 in a conformed configuration.

The above mentioned components may be made using materials and methods apparent to one of ordinary skill in the art. For example, elongated body 200, vascular closure device 230, and/or packing member 130 can be made of any material suitable for implantation within the body of the patient. Appropriate materials include synthetic materials and a grown or harvested tissue, such as an extracellular matrix material (ECM) such as porcine small intestinal submucosa (SIS). In some instances, spongy or foam materials or other forms of materials are used. Preparation of such materials is disclosed in U.S. patent application Ser. No. 12/489,199 (filed Jun. 22, 2009).

As noted above, in particular embodiments the material may be a collagenous extracellular matrix material such as SIS, and it is treated to partially denature and expand the native collagenous structure, for example with sodium hydroxide, to provide porosity and/or foam characteristics when dried. In certain embodiments, the extracellular matrix material can be processed to be medically acceptable while retaining a native collagenous microarchitecture (e.g. a native sheet form) and endogenous bioactive substances from an animal source tissue, such as a porcine, ovine, bovine or equine source tissue. Such endogenous substances can for example include one, some, or all of growth factors (e.g., Fibroblast Growth Factor-2), glycosaminoglycans, and proteoglycans. The extracellular matrix material can be treated with a chemical crosslinking agent, for example glutaraldehyde or a carbodiimide, to add crosslinks over and above any native crosslinks present, or can lack any such treatment. In other embodiments, elongated body 200, vascular closure device 230, and/or packing member 130 can comprise a reconstituted collagen sheet or foam, optionally crosslinked with a chemical crosslinker such as those discussed above.

The portions of system 100 that are not implanted into the body of the patient may be made of any number of materials.

For example, outer sheath 110, pushing member 132, insertion sheath 140, sleeve assembly 160, and/or introducer 240 may be made of plastic or other suitable material. In some instances the material may need to maintain its rigidity over a sufficient length (e.g., 10 to 20 cm or more), so that an operator may manipulate a proximal portion and impart movement of a distal portion, such as with pushing member 132. For example, when advancing packing member 130 with pushing member 132, the operator can manipulate such longer embodiments of pushing member 132 from outside of the patient, with tactile feedback indicated passage of packing member 130 and/or locking member 222 past protrusion 224 on elongated body 200.

Variations of the above described embodiments, as will be apparent to one of ordinary skill in the art, are contemplated by the present disclosure.

Use of system 100 will now be described with respect to closing and repairing an opening in a wall of a blood vessel. As noted previously, it is to be understood that similar usages can be made in other body tissues (e.g., bile or other ducts), or other vessels, conduits or walls. For example, in use with fistulae (e.g., vesciovaginal fistula), seal(s) as described herein may be placed and held over fistula openings and against tissue substantially as described below, with packing members within the fistula to assist with healing or correction of the fistula.

Figure 15:
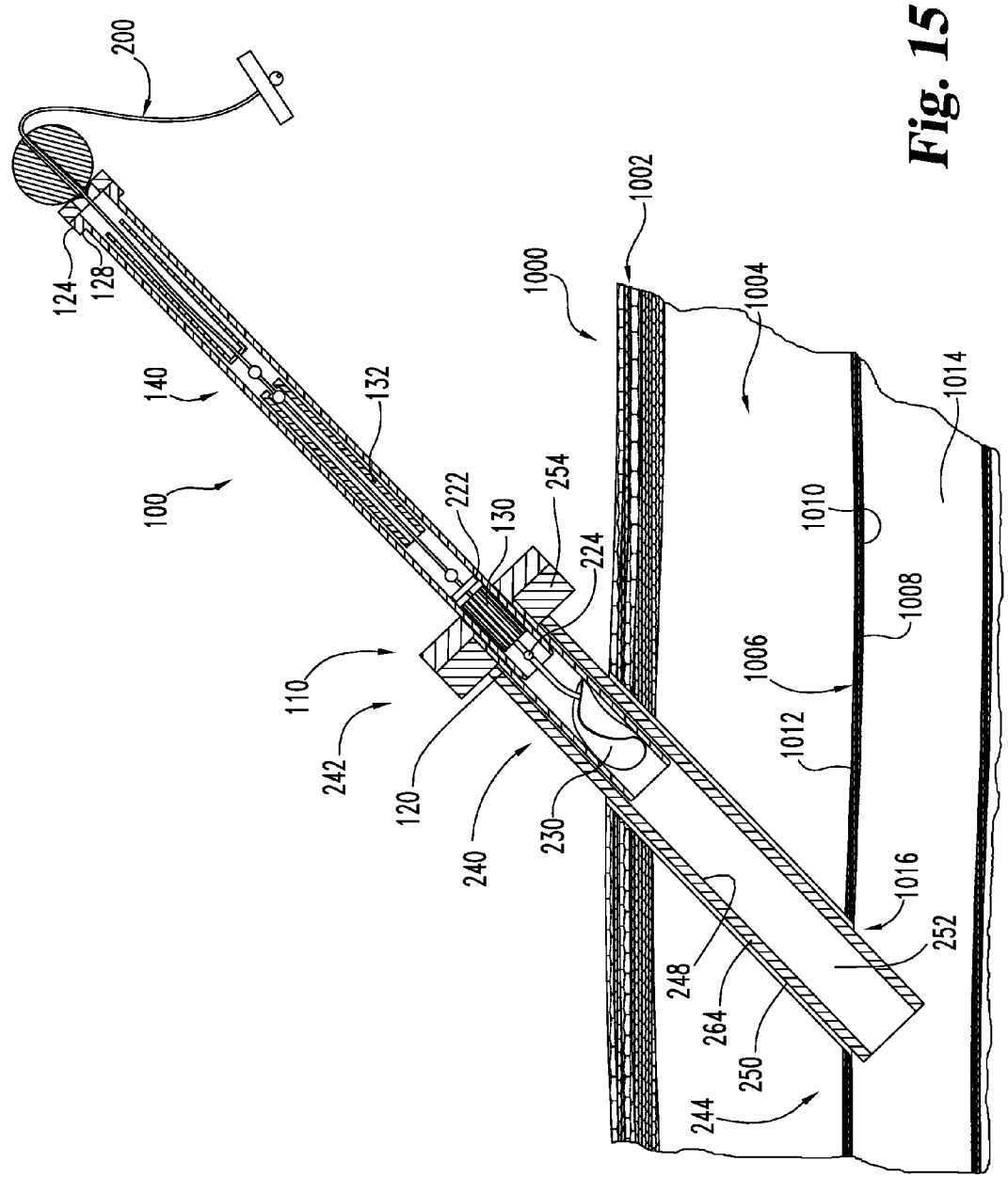
FIG. 15 is a cross-sectional view of the FIG. 1 system in a first position, with the sleeve assembly inserted into an introducer.

Reference to the following exemplary method of use will be made with regard to FIG. 15 illustrating vessel 1006 positioned beneath tissue 1000 such as skin 1002 and/or muscle/fat 1004 of the body of a patient. Vessel 1006 comprises vessel wall 1008 having inner surface 1010, outer surface 1012, and inner surface defining lumen 1014 extending through vessel 1006.

A surgeon or other medical professional performs and completes desired procedure(s) that involve access to blood vessel 1006 through hole 1016 in wall 1008 (e.g., balloon catheterization or stenting procedures). If a sheath, cannula or other access device or portal was used for the procedure(s), it can be left in vessel 1006, and system 100 described above may be inserted through it. If no such access device is present, or if a change of access device is advisable, introducer 240 may be placed in hole 1016 by using a dilator with an introducer sheath so that the distal end of introducer 240 is inside vessel 1006. Seal member 254 may provide a barrier preventing blood or other fluid from exiting through lumen 252 of introducer 240 from proximal end region 242.

Also as illustrated in FIG. 15, after access is gained to lumen 1014 of vessel 1006 within the body of the patient and vessel 1006 has been used to provide therapy and/or for diagnostic purposes, system 100, prepared as noted above, may be inserted into lumen 252 of introducer 240 and advanced distally towards vessel 1006. As outer surface 120 of outer sheath 110 slides along inner surface 248 defining lumen 252, distal surface 128 of flange 124 of outer sheath 110 contacts a portion of proximal end region 242 of introducer 240 and prevents further insertion of outer sheath 110 within lumen 252 of introducer 240.

Figure 16:
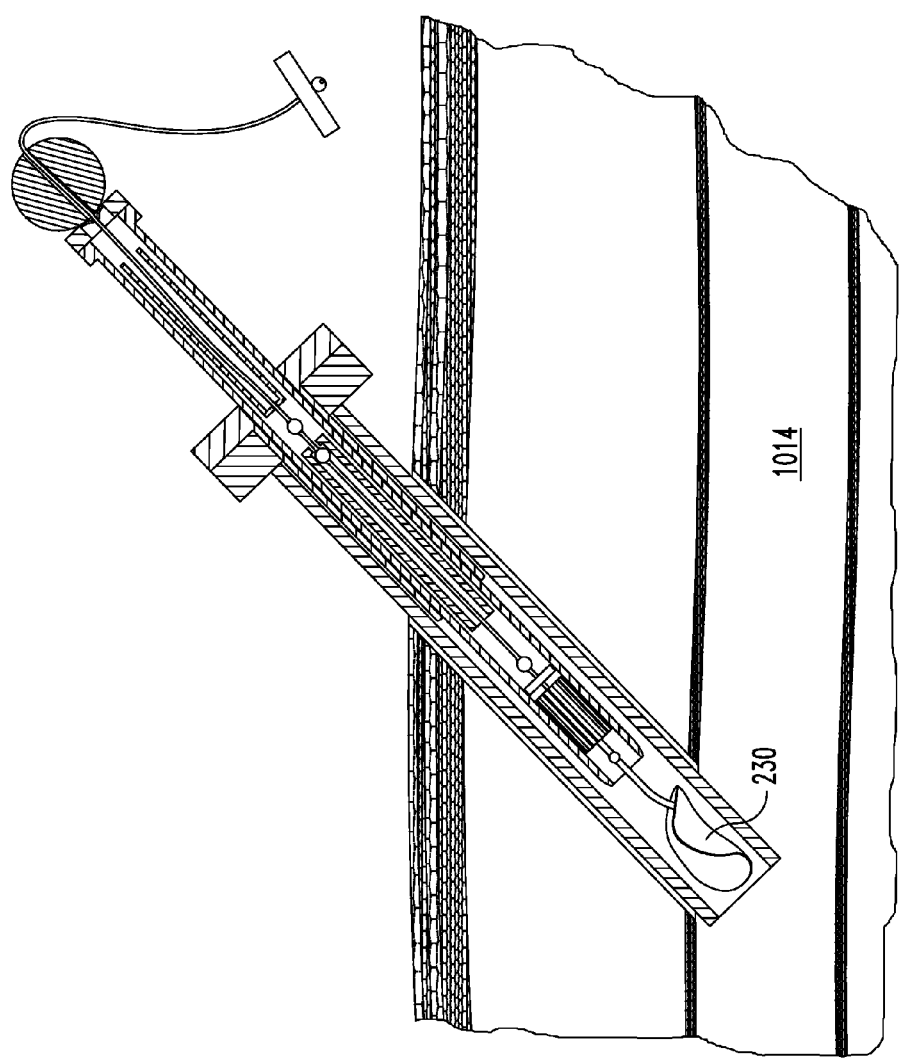
FIG. 16 is a cross-sectional view of the system illustrated in FIG. 15 in a second position, with the vascular closure device and insertion sheath advanced into the introducer.

If outer sheath 110 is shorter in length than introducer 240, then insertion sheath 140, elongated body 200 and the vascular closure device may be advanced through lumen 122 of outer sheath 110 so as to position vascular closure device 230 and/or portions of insertion sheath 140 and/or elongated body 200 within lumen 252 of introducer 240 as shown in FIG. 16.

Figure 17:
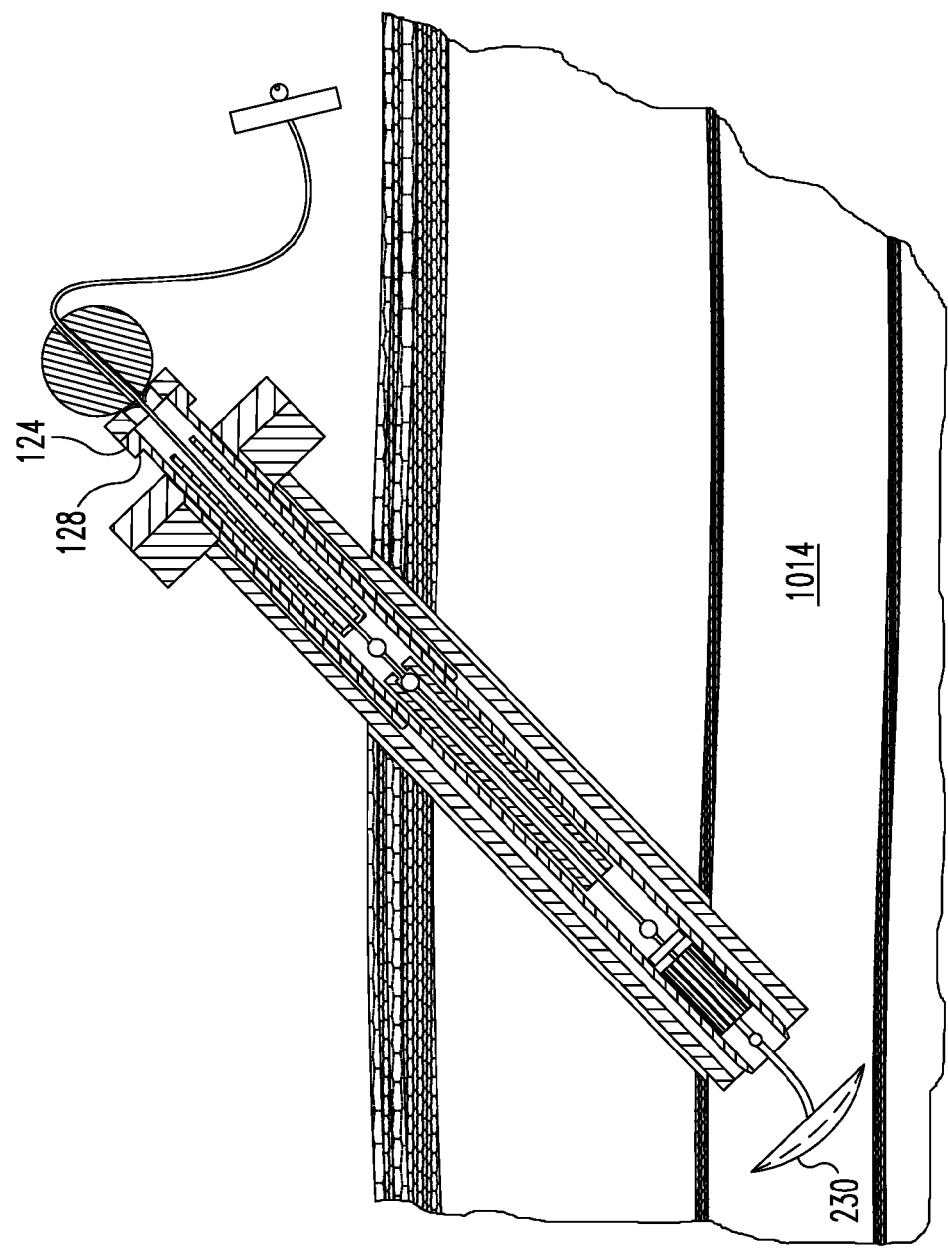
FIG. 17 is a cross-sectional view of the system illustrated in FIG. 15 in a third position, with the vascular closure device advanced out of the introducer into a lumen of a vessel.

As shown in FIG. 17, insertion sheath 140 may be advanced further so as to extend vascular closure device 230 out of lumen 252 and into lumen 1014 of vessel 1006, allowing vascular closure device 230 to expand into an expanded configuration within lumen 1014. After vascular closure device 230 has expanded into an expanded configuration, sleeve assembly 160, elongated body 200, and/or introducer 240 are/is withdrawn.

Figure 18:
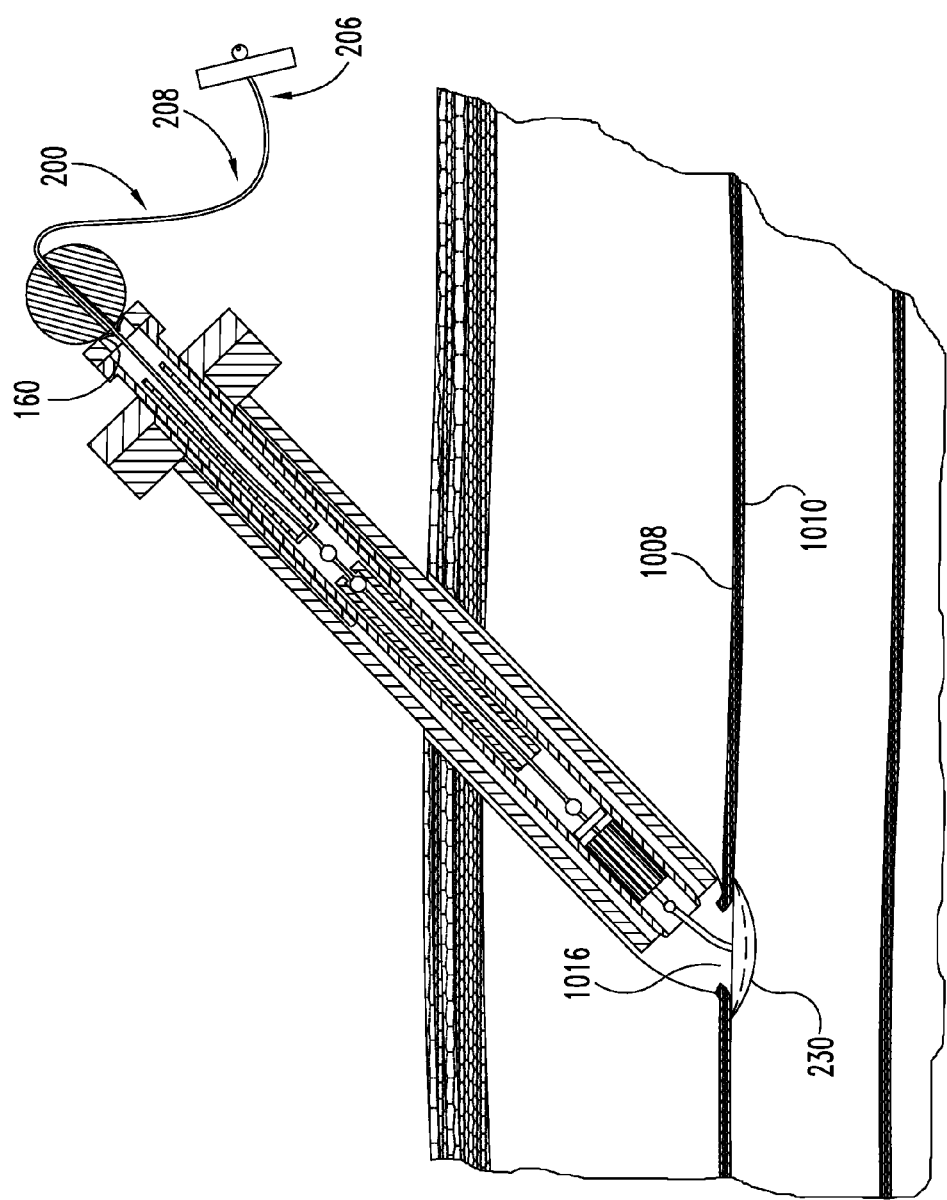
FIG. 18 is a cross-sectional view of the system illustrated in FIG. 15, in a fourth position, with the vascular closure device retracted and in contact with an inner surface of the vessel wall.

As shown in FIG. 18, as sleeve assembly 160 and/or introducer 240 are withdrawn from vessel 1006. As elongated body 200 is withdrawn from vessel 1006, vascular closure device 230 is pulled against inner surface 1010 of vessel wall 1008 thereby covering hole 1016 and elongated body 200 is pulled tight.

Figure 19:
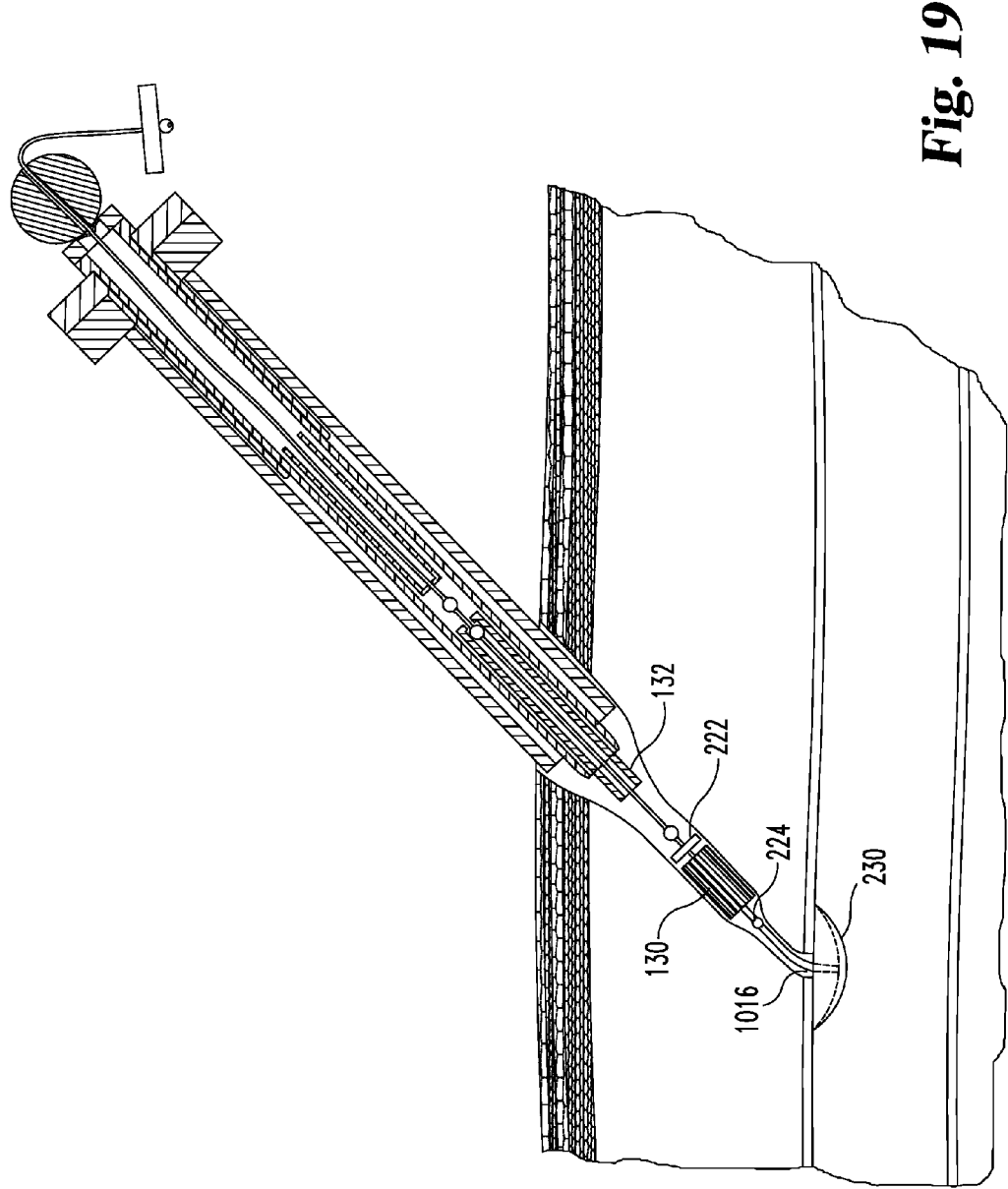
FIG. 19 is a cross-sectional view of the system illustrated in FIG. 15 in a fifth position, with the elongated body partially deployed out of the introducer vascular closure device.
Figure 20:
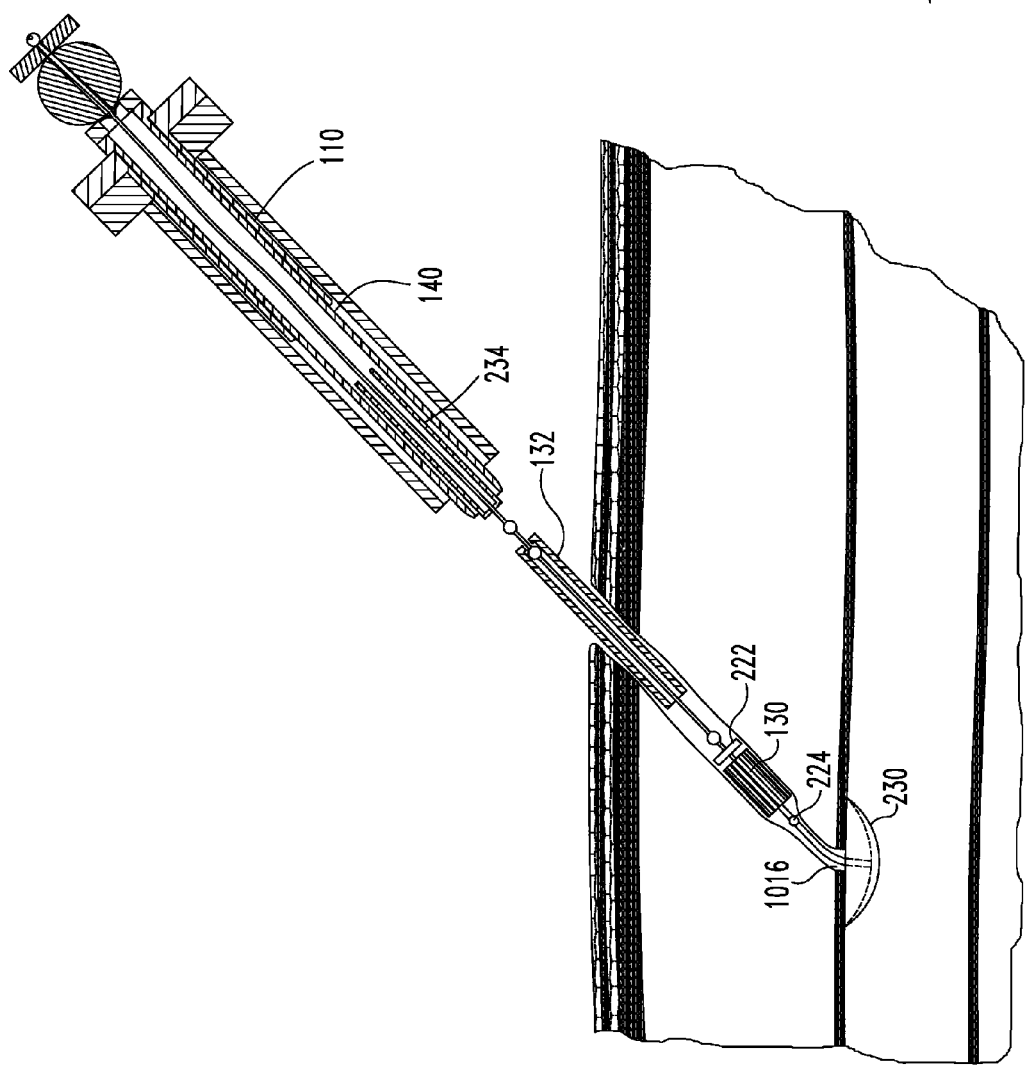
FIG. 20 is a cross-sectional view of the system illustrated in FIG. 15 in a sixth position, with the elongated body fully deployed out of the introducer.

As illustrated in FIGS. 19 and 20, the operator continues to withdraw sleeve assembly 160 and/or introducer 240 along the length of elongated body 200 until protrusion 210 abuts biasing member 180 and packing member 130, locking member 222 and pushing member 132 are fully deployed out of sleeve assembly 160 and/or introducer 240. In addition, indicator 234 is positioned near distal end region 114 of outer sheath 110.

Figure 21:
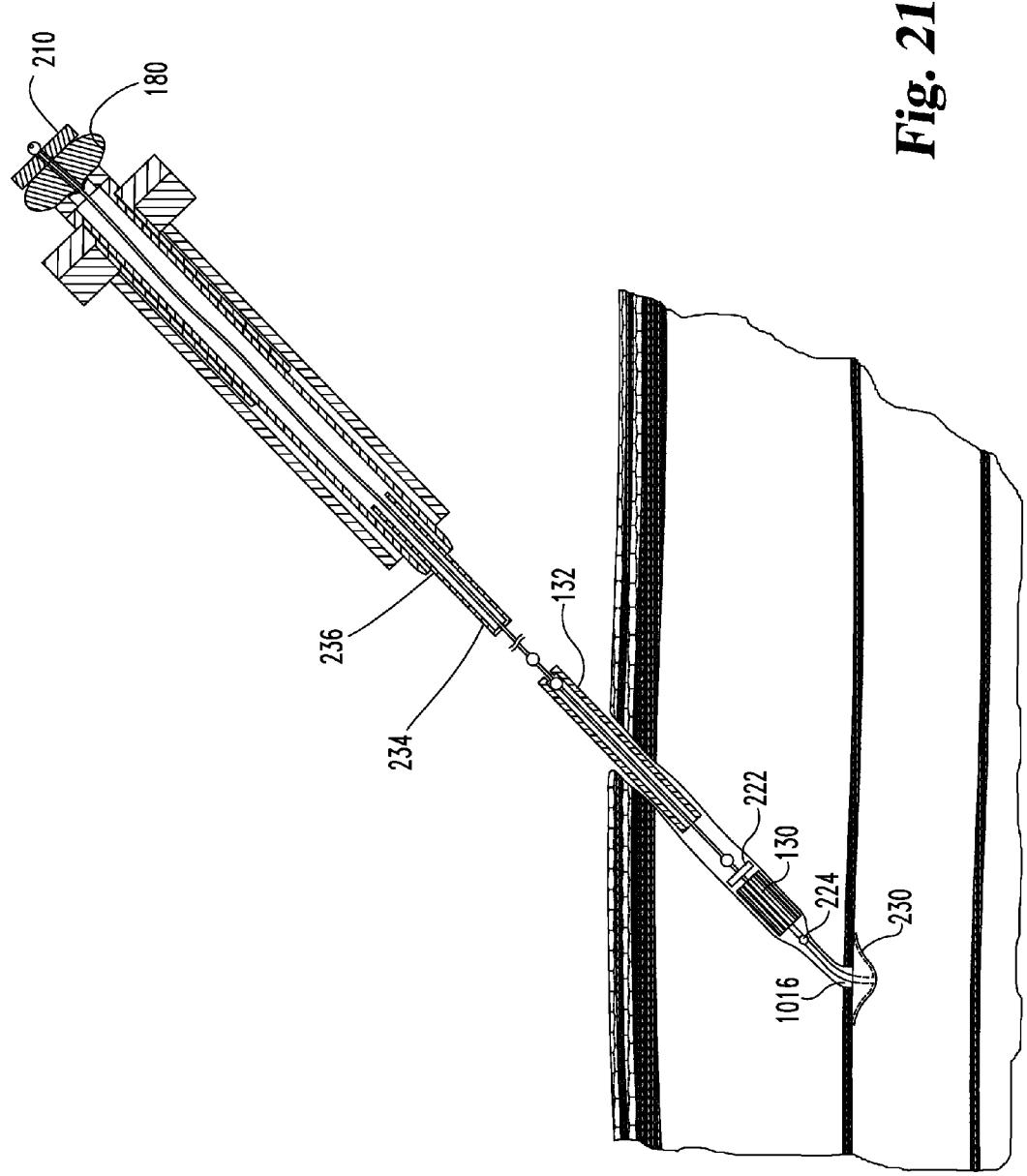
FIG. 21 is a cross-sectional view of the system illustrated in FIG. 15 in a seventh position, with tension applied to the elongated body placing the biasing member in compression and applying a conforming force to the vascular closure device through the elongated body.

As shown in FIG. 21, continued movement of sleeve assembly 160 and/or introducer 240 away from hole 1016 compresses biasing member 180 between protrusion 210 and proximal surface 156 of flange 154 on insertion sheath 140 and pulls vascular closure device 230 against inner surface 1010 deforming vascular closure device 230 to substantially seal hole 1016 against passage of a fluid such as blood through hole 1016. As biasing member 180 compresses, indicator 234 extends beyond distal end region 114 of outer sheath 110. Indicator 234 may provide an operator discernable visual evidence that a conforming force has been applied to vascular closure device 230. Furthermore, indicator 234 may include markings such as graduation markings including a conforming graduation 236 that indicates when a conforming force is applied to vascular closure device 230 through elongated body 200 and biasing member 180. Similarly, deformation of biasing member 180 may also provide discernable visual that a conforming force has been applied to vascular closure device 230.

Indicator 234 may be constructed and arranged such that it is substantially obscured when biasing member 180 is not compressed between protrusion 210 and proximal surface 156 but become discernible when a conforming force is applied to elongated body 200 through biasing member 180. Similarly, biasing member 180 may be constructed and arranged such that the amount of force required to compress a particular biasing member 180 is substantially equivalent to a conforming force for a particular vascular closure device 230.

Figure 22:
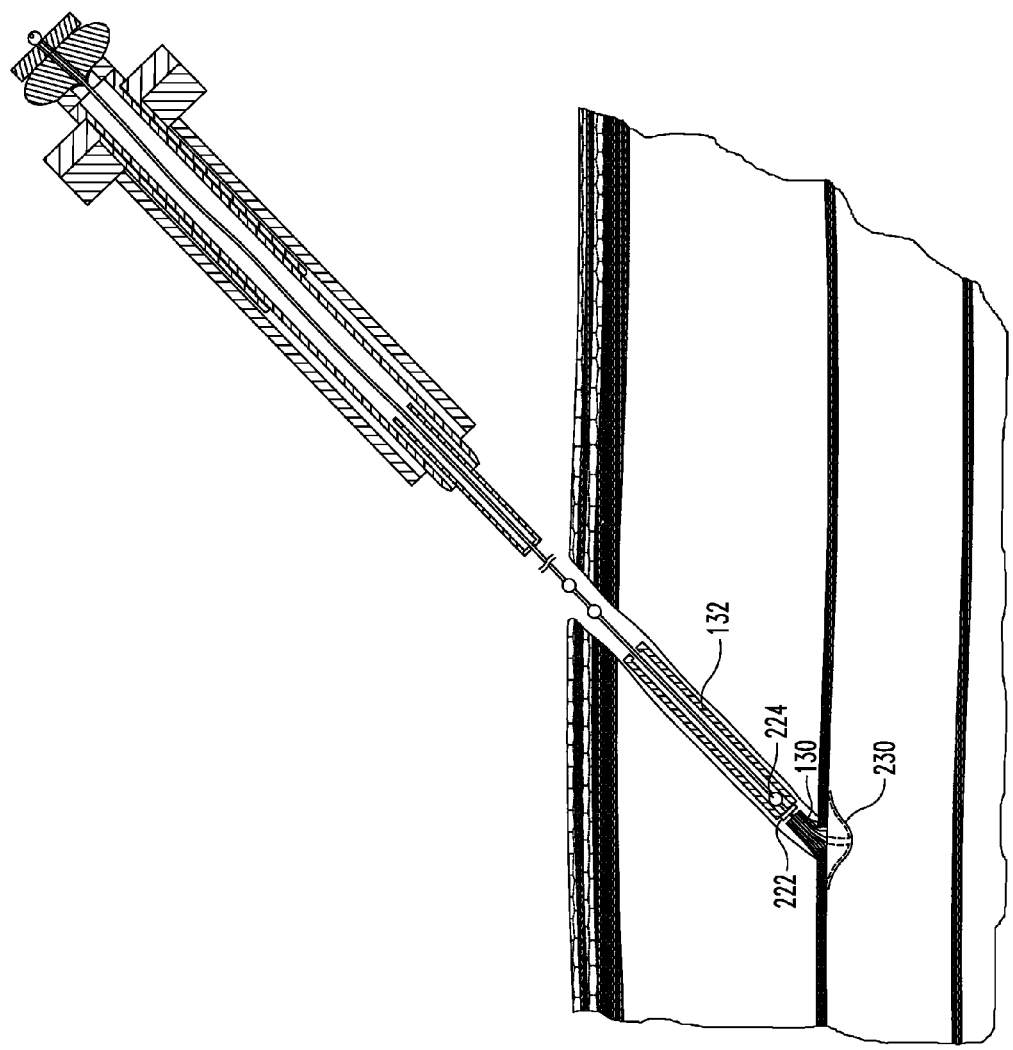
FIG. 22 is a cross-sectional view of the system illustrated in FIG. 15 in an eighth position, with the packing member advanced over the elongated body and abutting against the outer surface of the vessel wall.
Figure 23:
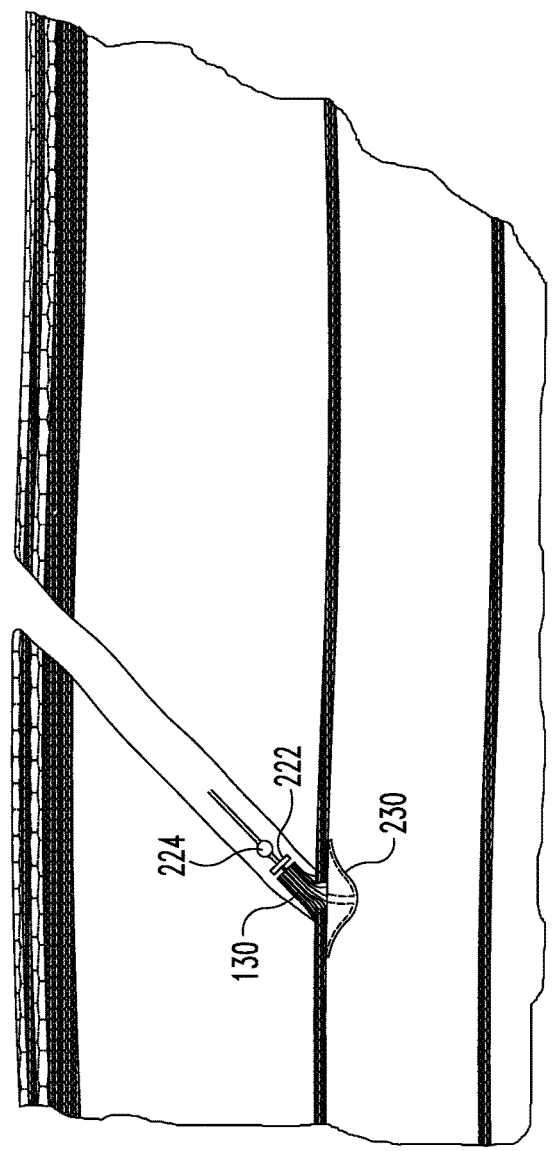
FIG. 23 is a cross-sectional view of the system illustrated in FIG. 15 in a ninth position, with the elongated body severed and removed, leaving the vascular closure device in situ.

Once the operator discerns that a conforming force has been applied to vascular closure device 230, the operator can inspect the treatment site to verify that fluid or blood flow through hole 1016 has been substantially stopped. If it has, the operator can proceed with completing the closure of hole 1016. While the operator continues to maintain the conforming force on vascular closure device 230, the operator advances packing member 130 and locking member 222 towards hole 1016 in vessel wall 1008 by advancing pushing member 132 along elongated body 200 until packing member 130 is compressed between outer surface 1012 of vessel wall 1008 and locking member 222 engages elongated body 200, for example, by passing over protrusion 224. This is illustrated in FIG. 22

When the operator is pleased with the positioning of packing member 130, such as when packing member 130 is coupled to the vessel 1006 by locking member 222, the operator severs elongated body 200 so as to leave vascular closure device 230 in position against inner surface 1010 of vessel wall 1008 with packing member 130 positioned against outer surface 1012 of vessel wall 1008 and a portion of elongated body 200 in tensions between vascular closure device 230 and locking member 222 with packing member 130 in-between. In this configuration, the portion of elongated body 200 left in situ continues to exert a conforming force on vascular closure device 230 and packing member 130 so as to substantially occlude hole 1016 in vessel wall 1008.

Figure 24:
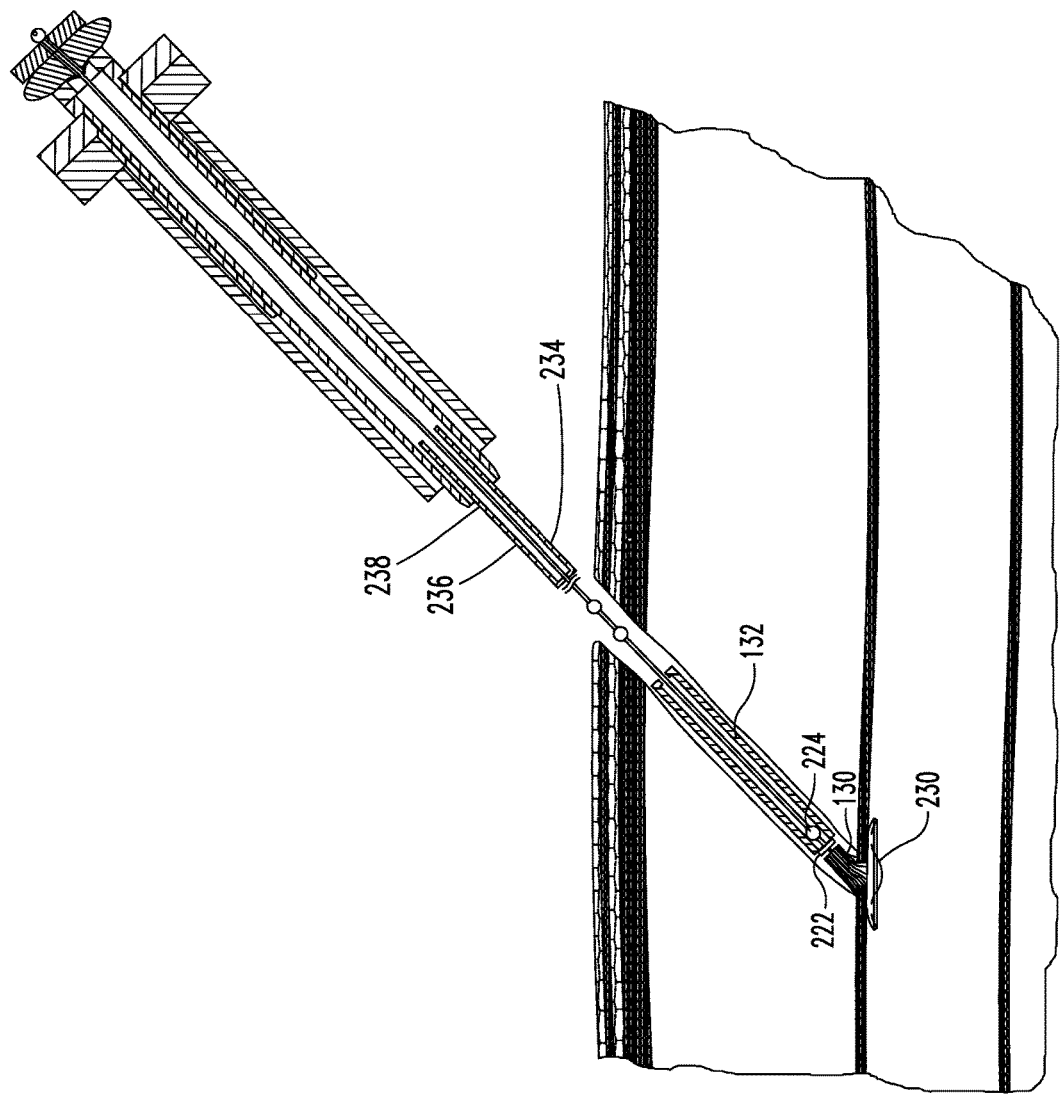
FIG. 24 is a cross-sectional view of the system illustrated in FIG. 15 in a tenth position, with tension applied to the elongated body placing the biasing member in compression and applying a deforming force to the vascular closure device through the elongated body.

FIG. 24 illustrates application of a deforming force. Indicator 234 may optionally include deforming graduation 238 that is located on indicator 234 to indicate when a deforming force greater than a conforming force and sufficient to deforming the vascular closure device such that it may not occlude hole 1016 is applied to vascular closure device through elongated body 200 and biasing member 180.

While other devices rely on a clot forming at the opening in the wall of the vessel, and thus result in substantial oozing from the opening while a clot is forming, embodiments such as those noted above cover the inside of the opening. Closure is maintained by tension on the seal, and by deforming the seal so that a portion of it is held against the vessel by the reaction of the seal to the deformation.

While the subject matter herein has been illustrated and described in detail in the exemplary drawings and foregoing description, the same is to be considered as illustrative and not restrictive in character, it being understood that only the preferred embodiment(s) have been shown and described and that all changes and modifications that come within the spirit of the disclosure are desired to be protected. It will be understood that structures, methods or other features described particularly with one embodiment can be similarly used or incorporated in or with respect to other embodiments.

The invention claimed is:

1. An apparatus for occluding a hole in a vessel wall, wherein an introducer defining a lumen passes through the hole from the outside of the vessel to the inside of the vessel, the apparatus comprising:
   an assembly having a predeployment state and a deployed state, said assembly comprising:
      a sleeve assembly defining a bore, wherein said sleeve assembly is adapted to be inserted into the lumen of the introducer;
      a pliant vascular closure device having a predeployment configuration wherein said pliant vascular closure device is deformed to fit within the bore of said sleeve assembly and a deployed state wherein said pliant vascular closure device is too large to fit within the bore of said sleeve assembly without deforming said pliant vascular closure device;
      an elongated body coupled to said pliant vascular closure device, said elongated body comprising a protrusion; and
      a biasing member connecting said elongated body to said sleeve assembly such that retracting said sleeve assembly away from said vascular closure device when said vascular closure device is deployed within the body of the patient moves said elongated body relative to said sleeve assembly until said protrusion contacts said biasing member, wherein further movement of said elongated body relative to said sleeve assembly elastically deforms said biasing member between said protrusion and said sleeve assembly, applies tension to said elongated body, and exerts a force on said vascular closure device.

2. The apparatus of claim 1, wherein application of a conforming force through said elongated body to said pliant vascular closure device deforms said pliant vascular closure device to conform against the vessel wall.

3. The apparatus of claim 2, wherein conforming said pliant vascular closure device against said vessel wall fluidly seals the hole in the vessel wall.

4. The apparatus of claim 2, further comprising an indicator coupled to said elongated body, wherein said indicator is positioned to be substantially obscured by said sleeve assembly when a force less than said conforming force is applied to said pliant vascular closure device through said elongated body and wherein said indicator is positioned to be discernible when said conforming force is applied to said pliant vascular closure device through said elongated body.

5. The apparatus of claim 1, wherein, in the deployed state, said pliant vascular closure device defines a symmetrical dome shape.

6. The apparatus of claim 1, wherein said sleeve assembly is adapted to be inserted into the lumen of the introducer located in the hole in the vessel wall and wherein said sleeve assembly is adapted to deploy said vascular closure device out of the introducer sheath into the vessel, wherein said sleeve assembly is adapted to be withdrawn from the hole with the introducer sheath, wherein said sleeve assembly further comprises a flange adapted to abut the introducer sheath and block the sleeve assembly from passing through the introducer sheath such that the introducer sheath may be used as a grip to retract said sleeve assembly away from said vascular closure device.

7. The apparatus of claim 6, wherein said elongated body extends through the introducer when tension is applied to said elongated body by retracting said sleeve assembly away from said pliant vascular closure device.

8. The apparatus of claim 1, wherein said biasing member is positioned on the proximal end of the sleeve assembly with the elongated body extending through said biasing member and said sleeve assembly, wherein said biasing member is constructed and arranged to longitudinally compress when tension is applied to said elongated body by retracting said sleeve assembly away from said pliant vascular closure device.

9. The apparatus of claim 1, wherein, inserting the sleeve assembly into the lumen of the introducer in the predeployment state, positions the pliant vascular closure device within the lumen of the introducer.

10. The apparatus of claim 1, wherein the sleeve assembly comprises an outer sheath that defines an outer sheath lumen and an insertion sheath positioned within the outer sheath lumen, wherein the insertion sheath moves relative to the outer sheath when moving from the predeployment state to the deployed state.

11. An apparatus for occluding a hole in a vessel wall, wherein an introducer defining a lumen passes through the hole from the outside of the vessel to the inside of the vessel, the apparatus comprising:
   an assembly having a predeployment state and a deployed state, said assembly comprising:
      a sleeve assembly defining a bore, wherein said sleeve assembly is adapted to be inserted into the lumen of the introducer;
      a pliant vascular closure device having a predeployment configuration wherein said pliant vascular closure device is deformed to fit within the bore of said sleeve assembly and a deployed state wherein said pliant vascular closure device is too large to fit within the bore of said sleeve assembly without deforming said pliant vascular closure device;

an elongated body coupled to said pliant vascular closure device; and a biasing member connecting said elongated body to said sleeve assembly such that retracting said sleeve assembly away from said vascular closure device when said vascular closure device is deployed within the body of the patient applies tension to said elongated body and elastically deforms said biasing member and exerts a force on said vascular closure device, wherein said biasing member is positioned on the proximal end of said elongated body with the biasing member extending through said sleeve assembly, wherein said biasing member is constructed and arranged to lengthen longitudinally when tension is applied to said elongated body by retracting said sleeve assembly away from said pliant vascular closure device.

12. An apparatus for occluding a hole in a vessel wall of a vessel, wherein an introducer defining a lumen passes through the hole from the outside of the vessel to the inside of the vessel, the apparatus comprising:

an assembly having a predeployment state and a deployed state, said assembly comprising:

a sleeve assembly defining a bore, wherein said sleeve assembly is adapted to be inserted into the lumen of the introducer;

a pliant vascular closure device;

an elongated body coupled to said pliant vascular closure device, said elongated body comprising a protrusion; and a biasing member connecting said elongated body to said sleeve assembly such that retracting said sleeve assembly away from said vascular closure device when said vascular closure device is deployed within the body of the patient moves said elongated body relative to said sleeve assembly until said protrusion contacts said biasing member, wherein further movement of said elongated body relative to said sleeve assembly elastically deforms said biasing member between said protrusion and said sleeve assembly, applies tension to said elongated body, and exerts a force on said vascular closure device, and wherein application of a conforming force through said elongated body to said pliant vascular closure device deforms said pliant vascular closure device to conform against the vessel wall.

13. The apparatus of claim 12, wherein conforming said pliant vascular closure device against said vessel wall fluidly seals the hole in the vessel wall.

14. The apparatus of claim 12, further comprising an indicator coupled to said elongated body, wherein said indicator is positioned to be substantially obscured by said sleeve assembly when a force less than said conforming force is applied to said pliant vascular closure device through said elongated body and wherein said indicator is positioned to be discernible when said conforming force is applied to said pliant vascular closure device through said elongated body.

15. The apparatus of claim 12, wherein, in the deployed state, said pliant vascular closure device defines a symmetrical dome shape.

16. The apparatus of claim 12, wherein said sleeve assembly is adapted to be inserted into the lumen of the introducer located in the hole in the vessel wall and wherein said sleeve assembly is adapted to deploy said vascular closure device out of the introducer sheath into the vessel, wherein said sleeve assembly is adapted to be withdrawn from the hole with the introducer sheath, wherein said sleeve assembly further comprises a flange adapted to abut the introducer sheath and block the sleeve assembly from passing through the introducer sheath such that the introducer sheath may be used as a grip to retract said sleeve assembly away from said vascular closure device.

17. The apparatus of claim 16, wherein said elongated body extends through the introducer when tension is applied to said elongated body by retracting said sleeve assembly away from said pliant vascular closure device.

18. The apparatus of claim 12, further comprising a packing member arranged on said elongated member and constructed and arranged to be longitudinally displaced with respect to said elongated member to abut the vessel wall, wherein said packing member comprises a material suitable for implantation within the body of a patient while abutting the vessel wall.

19. The apparatus of claim 18, wherein conforming said pliant vascular closure device against said vessel wall fluidly seals the hole in the vessel wall before said packing member abuts the vessel wall.

20. An apparatus for occluding a hole in a vessel wall of a vessel, wherein an introducer defining a lumen passes through the hole from the outside of the vessel to the inside of the vessel, the apparatus comprising:

an assembly having a predeployment state and a deployed state, said assembly comprising:

a sleeve assembly defining a bore, wherein said sleeve assembly is adapted to be inserted into the lumen of the introducer;

a pliant vascular closure device;

an elongated body coupled to said pliant vascular closure device, said elongated body comprising a protrusion; and a biasing member connecting said elongated body to said sleeve assembly such that retracting said sleeve assembly away from said vascular closure device when said vascular closure device is deployed within the body of the patient moves said elongated body relative to said sleeve assembly until said protrusion contacts said biasing member, wherein further movement of said elongated body relative to said sleeve assembly elastically deforms said biasing member between said protrusion and said sleeve assembly, applies tension to said elongated body, and exerts a force on said vascular closure device; wherein application of a conforming force through said elongated body to said pliant vascular closure device deforms said pliant vascular closure device to conform against the vessel wall, wherein said sleeve assembly is adapted to be inserted into the lumen of the introducer located in the hole in the vessel wall and wherein said sleeve assembly is adapted to deploy said vascular closure device out of the introducer sheath into the vessel, wherein said sleeve assembly is adapted to be withdrawn from the hole with the introducer sheath, and wherein said sleeve assembly further comprises a flange adapted to abut the introducer sheath and block the sleeve assembly from passing through the introducer sheath such that the introducer sheath may be used as a grip to retract said sleeve assembly away from said vascular closure device.

21. The apparatus of claim 20, wherein conforming said pliant vascular closure device against said vessel wall fluidly seals the hole in the vessel wall.

22. The apparatus of claim 20, further comprising an indicator coupled to said elongated body, wherein said indicator is positioned to be substantially obscured by said sleeve assembly when a force less than said conforming force is applied to said pliant vascular closure device through said elongated body and wherein said indicator is positioned to be discernible when said conforming force is applied to said pliant vascular closure device through said elongated body.

* * * * *